(12) United States Patent
Seegert et al.

(10) Patent No.: US 7,851,182 B2
(45) Date of Patent: *Dec. 14, 2010

(54) SOLUBLE GP130 MOLECULE VARIANTS USEFUL AS A MEDICAMENT

(75) Inventors: Dirk Seegert, Danischenhagen (DE); Georg H. Waetzig, Kiel (DE)

(73) Assignee: Conaris Research Institute AG, Kiel (DE)

( * ) Notice: Subject to any disclaimer, the term of this patent is extended or adjusted under 35 U.S.C. 154(b) by 42 days.

This patent is subject to a terminal disclaimer.

(21) Appl. No.: 12/158,285

(22) PCT Filed: Dec. 22, 2006

(86) PCT No.: PCT/EP2006/012515
§ 371 (c)(1),
(2), (4) Date: Oct. 20, 2008

(87) PCT Pub. No.: WO2007/071449
PCT Pub. Date: Jun. 28, 2007

(65) Prior Publication Data
US 2009/0227499 A1    Sep. 10, 2009

(30) Foreign Application Priority Data
Dec. 23, 2005    (EP)    ................. 05028420

(51) Int. Cl.
| | |
|---|---|
| *C12N 15/09* | (2006.01) |
| *C12N 15/11* | (2006.01) |
| *C12N 15/12* | (2006.01) |
| *C12N 15/63* | (2006.01) |
| *C12N 1/20* | (2006.01) |
| *C12N 1/15* | (2006.01) |
| *C12N 5/07* | (2006.01) |
| *C07K 14/00* | (2006.01) |
| *C07K 14/435* | (2006.01) |

(52) U.S. Cl. ................. 435/69.1; 435/69.7; 435/325; 435/348; 435/252.3; 435/254.11; 435/320.1; 536/23.1; 536/23.4; 536/23.5; 530/350; 530/351; 514/2

(58) Field of Classification Search ................. None
See application file for complete search history.

(56) References Cited

U.S. PATENT DOCUMENTS

| | | | |
|---|---|---|---|
| 7,534,862 B2 * | 5/2009 | Seegert et al. ................. 530/350 |
| 7,629,147 B2 * | 12/2009 | Seegert et al. ................. 435/69.1 |
| 2002/0169292 A1 * | 11/2002 | Weintraub et al. ................. 530/397 |

FOREIGN PATENT DOCUMENTS

| | | |
|---|---|---|
| EP | 1148065 | 10/2001 |
| EP | 1491554 A1 | 12/2004 |
| WO | WO94/12520 A1 | 6/1994 |

OTHER PUBLICATIONS

Chow, Dar-Chone, et al., "A structural template for gp130-cytokine signaling assemblies", Biochimica et Biophysica Acta, vol. 1592, No. 3, Nov. 11, 2002, pp. 225-235.
Giese, Bernd, et al., "Dimerization of the cytokine receptors gp130 and LIFR analysed in single cells", Journal of Cell Science, vol. 118, No. 21, Nov. 2005, pp. 5129-5140.
Ward, Larry D., et al., "Influence of Interleukin-6 (IL-6) Dimerization on Formation of the High Affinity Hexameric IL-6 Receptor Complex", The Journal of Biological Chemistry, vol. 271, No. 33, Aug. 16, 1996, pp. 20138-20144.
International Search Report for PCT/EP2006/012515, mailed May 4, 2007.

* cited by examiner

*Primary Examiner*—Elizabeth C. Kemmerer
(74) *Attorney, Agent, or Firm*—Howrey LLP; Viola T. Kung

(57) ABSTRACT

A polypeptide-dimer built of two identical monomeric fragments comprising the domains 1 to 3 of the extracellular (soluble) part of glycoprotein (gp)130 and a certain polypeptide spacer are described, which are covalently linked with each other and which bear significant advantages concerning their production rate in host cells, their improved purification and their potential to bind to IL-6/soluble IL-6 receptor complexes. Furthermore, a pharmaceutical composition containing said dimeric molecule and various medical uses are described.

20 Claims, 8 Drawing Sheets sgp130Fc (parental molecule)

Construct: pcDNA-DEST40_sgp130Fc, stable line in CHO-K1
Sample pre-purified on MAbSelect-AC, Gelfiltration: Superdex-GF
SDS PAGE, staining: Coomassie/Imperial Stain („COOM.") and silver sgp130(D1-D3)S$_1$-Fc

Construct: pcDNA-DEST40_ sgp130(D1-D3)S$_1$-Fc, stable line in CHO-K1
Sample pre-purified on MAbSelect-AC, Gelfiltration: Superdex-GF
SDS PAGE, staining: Coomassie/Imperial Stain („COOM.") and silver

Codon-optimized cDNA sequence of sgp130(D1-D3):

```
  1    ATGCTGACACTGCAGACATGGCTGGTGCAGGCCCTGTTTATCTTTCTGAC
 51    CACCGAGTCTACAGGAGAGCTGCTGGATCCTTGCGGCTATATCTCCCCTG
101    AGTCTCCTGTGGTGCAGCTGCATTCTAACTTCACCGCCGTGTGTGTGCTG
151    AAGGAAAAGTGCATGGACTACTTCCACGTGAACGCCAACTACATCGTGTG
201    GAAAACCAACCACTTCACCATCCCCAAGGAGCAGTACACCATCATCAACC
251    GGACCGCTTCTTCTGTGACCTTCACCGATATCGCCTCCCTGAATATCCAG
301    CTGACCTGCAACATCCTGACCTTTGGACAGCTGGAGCAGAATGTGTACGG
351    CATCACCATCATCTCTGGCCTGCCTCCAGAGAAGCCTAAGAACCTGTCCT
401    GCATCGTGAATGAGGGCAAGAAGATGAGGTGTGAGTGGGATGGCGGCAGA
451    GAGACACATCTGGAGACCAACTTCACCCTGAAGTCTGAGTGGGCCACCCA
501    CAAGTTTGCCGACTGCAAGGCCAAGAGAGATACCCCTACCTCTTGCACCG
551    TGGACTACTCCACCGTGTACTTCGTGAACATCGAGGTGTGGGTGGAGGCT
601    GAGAATGCTCTGGGCAAGGTGACCTCTGACCACATCAACTTCGACCCCGT
651    GTACAAGGTGAAGCCTAACCCTCCTCACAACCTGTCCGTGATCAACTCTG
701    AGGAGCTGTCCTCTATCCTGAAGCTGACCTGGACCAACCCTTCCATCAAG
751    TCCGTGATCATCCTGAAGTACAACATCCAGTACAGGACCAAGGATGCTTC
801    TACCTGGTCTCAGATCCCTCCTGAGGATACCGCTTCCACCAGATCCAGCT
851    TCACAGTGCAGGACCTGAAGCCTTTTACCGAGTACGTGTTCAGGATCCGG
901    TGCATGAAGGAGGATGGCAAGGGCTATTGGTCTGACTGGTCTGAGGAGGC
951    TTCTGGCATCACCTACGAGGAC   (972 bp)
```

Figure 7

Polypeptide sequence of sgp130(D1-D3):

```
  1    MLTLQTWLVQALFIFLTTESTGELLDPCGYISPESPVVQLHSNFTAVCVL
 51    KEKCMDYFHVNANYIVWKTNHFTIPKEQYTIINRTASSVTFTDIASLNIQ
101    LTCNILTFGQLEQNVYGITIISGLPPEKPKNLSCIVNEGKKMRCEWDGGR
151    ETHLETNFTLKSEWATHKFADCKAKRDTPTSCTVDYSTVYFVNIEVWVEA
201    ENALGKVTSDHINFDPVYKVKPNPPHNLSVINSEELSSILKLTWTNPSIK
251    SVIILKYNIQYRTKDASTWSQIPPEDTASTRSSFTVQDLKPFTEYVFRIR
301    CMKEDGKGYWSDWSEEASGITYED (324 aa)
```

Figure 8

SEQUENCE LISTING

<160> NUMBER OF SEQ ID NOS: 4

<210> SEQ ID NO 1
<211> LENGTH: 6
<212> TYPE: PRT
<213> ORGANISM: artificial
<220> FEATURE:
<223> OTHER INFORMATION: His-Tag

<400> SEQUENCE: 1

His His His His His His
1               5

<210> SEQ ID NO 2
<211> LENGTH: 5
<212> TYPE: PRT
<213> ORGANISM: artificial
<220> FEATURE:
<223> OTHER INFORMATION: spacer sequence

<400> SEQUENCE: 2

Gly Gly Gly Gly Ser
1               5

<210> SEQ ID NO 3
<211> LENGTH: 972
<212> TYPE: DNA
<213> ORGANISM: artificial
<220> FEATURE:
<223> OTHER INFORMATION: cDNA of sgp130(D1-D3)

<400> SEQUENCE: 3

```
atgctgacac tgcagacatg gctggtgcag gccctgttta tctttctgac caccgagtct      60
acaggagagc tgctggatcc ttgcggctat atctcccctg agtctcctgt ggtgcagctg     120
cattctaact tcaccgccgt gtgtgtgctg aaggaaaagt gcatggacta cttccacgtg     180
aacgccaact acatcgtgtg gaaaaccaac cacttccacca tccccaagga gcagtacacc     240
atcatcaacc ggaccgcttc ttctgtgacc ttcaccgata tcgcctccct gaatatccag     300
ctgacctgca catcctgac ctttggacag ctggagcaga atgtgtacgg catcaccatc      360
atctctggcc tgcctccaga gaagcctaag aacctgtcct gcatcgtgaa tgagggcaag     420
aagatgaggt gtgagtggga tgcggcagaa gagacacatc tggagaccaa cttcacccctg    480
aagtctgagt gggccaccca caagtttgcc gactgcaagg ccaagagaga tacccctacc     540
tcttgcaccg tggactactc caccgtgtac ttcgtgaaca tcgaggtgtg ggtggaggct     600
gagaatgctc tgggcaaggt gacctctgac cacatcaact tcgacccgt gtacaaggtg      660
aagcctaacc ctcctcacaa cctgtccgtg atcaactctg aggagctgtc ctctatcctg     720
aagctgacct ggaccaaccc cttccatcaag tccgtgatca tcctgaagta caacatccag    780
tacaggacca aggatgcttc tacctggtct cagatccctc ctgaggatac cgcttccacc     840
agatccagct tcacagtgca ggacctgaag ccttttaccg agtacgtgtt caggatccgg     900
tgcatgaagg aggatggcaa gggctattgg tctgactggt ctgaggaggc ttctggcatc     960
acctacgagg ac                                                          972
```

<210> SEQ ID NO 4
<211> LENGTH: 324
<212> TYPE: PRT
<213> ORGANISM: artificial
<220> FEATURE:
<223> OTHER INFORMATION: sgp130(D1-D3)

<400> SEQUENCE: 4

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

-continued

```
Val Leu Lys Glu Lys Cys Met Asp Tyr Phe His Val Asn Ala Asn Tyr
    50              55              60
Ile Val Trp Lys Thr Asn His Phe Thr Ile Pro Lys Glu Gln Tyr Thr
65              70              75              80
Ile Ile Asn Arg Thr Ala Ser Ser Val Thr Phe Thr Asp Ile Ala Ser
                85              90              95
Leu Asn Ile Gln Leu Thr Cys Asn Ile Leu Thr Phe Gly Gln Leu Glu
            100             105             110
Gln Asn Val Tyr Gly Ile Thr Ile Ile Ser Gly Leu Pro Pro Glu Lys
        115             120             125
Pro Lys Asn Leu Ser Cys Ile Val Asn Glu Gly Lys Lys Met Arg Cys
    130             135             140
Glu Trp Asp Gly Gly Arg Glu Thr His Leu Glu Thr Asn Phe Thr Leu
145             150             155             160
Lys Ser Glu Trp Ala Thr His Lys Phe Ala Asp Cys Lys Ala Lys Arg
                165             170             175
Asp Thr Pro Thr Ser Cys Thr Val Asp Tyr Ser Thr Val Tyr Phe Val
            180             185             190
Asn Ile Glu Val Trp Val Glu Ala Glu Asn Ala Leu Gly Lys Val Thr
        195             200             205
Ser Asp His Ile Asn Phe Asp Pro Val Tyr Lys Val Lys Pro Asn Pro
    210             215             220
Pro His Asn Leu Ser Val Ile Asn Ser Glu Glu Leu Ser Ser Ile Leu
225             230             235             240
Lys Leu Thr Trp Thr Asn Pro Ser Ile Lys Ser Val Ile Ile Leu Lys
                245             250             255
Tyr Asn Ile Gln Tyr Arg Thr Lys Asp Ala Ser Thr Trp Ser Gln Ile
            260             265             270
Pro Pro Glu Asp Thr Ala Ser Thr Arg Ser Ser Phe Thr Val Gln Asp
        275             280             285
Leu Lys Pro Phe Thr Glu Tyr Val Phe Arg Ile Arg Cys Met Lys Glu
    290             295             300
Asp Gly Lys Gly Tyr Trp Ser Asp Trp Ser Glu Glu Ala Ser Gly Ile
305             310             315             320
Thr Tyr Glu Asp
```

SOLUBLE GP130 MOLECULE VARIANTS USEFUL AS A MEDICAMENT

This application is a National Stage of International Application PCT/EP2006/012515, filed Dec. 22, 2006, published Jun. 28, 2007, under PCT Article 21(2) in English; which claims the priority of Application No. EP05028420.7, filed Dec. 23, 2005.

A polypeptide-dimer built of two identical monomeric fragments comprising the domains 1 to 3 of the extracellular (soluble) part of glycoprotein (gp)130 and a particular polypeptide spacer are described, which are covalently linked with each other and which bear significant advantages concerning their production rate in host cells, their improved purification and their potential to bind to IL-6/soluble IL-6 receptor complexes. Furthermore, a pharmaceutical composition containing said dimeric molecule and various medical uses are described.

The pleiotropic cytokine interleukin-6 (IL-6) shows a wide spectrum of biological functions among which stimulation of B and T cells, the control of acquired and innate immune processes and the induction of acute phase protein synthesis in liver are mostly notable. IL-6 exerts its activity via a membrane-bound or a soluble IL-6 receptor ("IL-6R" or "gp80") which upon binding induces the dimerization of gp130 to trigger cellular responses.

Since the cytoplasmic domain of IL-6R lacks kinase activity, signalling by gp130 homodimer can be induced by IL-6 in complex with membrane-bound or soluble IL-6R. While gp130 can be found on nearly every cell type, IL-6R expression is restricted to hepatocytes and leukocytes. However, these cells can be activated by IL-6 via sIL-6R which is released from IL-6R expressing cells either by proteolytic cleavage or alternative splicing. This mechanism is called trans-signalling. Indeed, several cellular activities have been shown which are dependent on the complex of sIL-6R plus IL-6 and are not inducible by IL-6 alone.

Trans-signalling plays a key role in the switch from innate to acquired immune responses and is crucial for the clearance of neutrophilic infiltrates and the recruitment and activation of T and B cells for a sustained immunological answer. Dysregulation of this mechanism leads to the development and persistence of chronic and/or allergic inflammatory disease such as Crohn's disease, rheumatoid arthritis, asthma and others.

For the treatment of these diseases, the specific blockade of IL-6-mediated processes has been shown to be therapeutically effective. Unfortunately, all compounds currently available for this purpose so far bear the problem of partly severe side-effects (e.g. secondary infections, tuberculosis, sepsis), toxicity or immunogenicity. Additionally, unsoluble difficulties have also been observed during the development of a useful and economic purification procedure.

The solution of said technical problems is achieved by providing the embodiments characterized in the claims. During the experiments leading to the present invention it was found that the purification of the parental compound sgp130Fc comprising two molecules of the entire extracellular part of gp130 was unsatisfying. This fusion protein, if expressed in eukaryotic CHO cells tends to build undesired side products such as certain smaller fragments, oligomers and aggregates in diverse combinations. It was not possible to find any kind of purification method which was suitable to separate the target compound from these impurities at adequate amounts due to very similar chemical and physical properties of the impurities and the core product. Among the tested methods were different affinity, size exclusion and ion exchange chromatographies, approaches to change the solubility of the protein by ion supplementation or pH shift and others. None of these methods was providing satisfying results or was suitable for an upscaling to develop a GMP compliant purification process. In contrast it was found that a shorter variant of the parental molecule sgp130Fc, called sgp130(D1-3)Fc, which was lacking the extracellular domains 4 to 6 was well separable from impurifying side products. This indicated that aggregate forming elements within the fibronectin III domains (domains 4 to 6) of the parental sgp130Fc molecule were successfully eliminated. Moreover, this molecule was expressed by eukaryotic cells at remarkably higher rates.

In the next step the efficiency of the new molecule sgp130 (D1-3)Fc to bind to IL-6/sIL-6R was optimized by fusing polypeptide spacers of different length between the sgp130 (D1-3) and the IgG-Fc part. The binding skills of the resulting molecules were determined by specific enzyme-linked immunosorbent assays (ELISA) and compared to the parental molecule sgp130Fc (FIG. 5).

Binding of IL-6/sIL-6R complexes has been shown to inhibit the anti-apoptotic effect of IL-6 on monocytes in Crohn's disease patients indicating that such compound is useful for the treatment of said disease and related diseases such as colitis, rheumatoid arthritis, psoriasis, peritonitis and others.

Crohn's disease is a chronic inflammatory disorder of the entire gastrointestinal tract characterized by frequently occurring relapses of acute inflammation. Inflammation associated with infection, injury, and other factors rapidly induces the acute phase reaction (APR) accompanied by the expression of acute phase proteins (APPs). The APR mainly results in an increase of vascular permeability and fever. IL-6 family members upregulate the expression of type II APP genes which is mediated by the (STAT3). Strong activation of STAT3 (i.e. tyrosine phosphorylation) has been described in colonic tissues from inflammatory bowel disease (IBD) patients. Moreover, reduced STAT3 activity was observed in IL-6$^{-/-}$ mice which was associated with a reduced development of experimental murine colitis (Suzuki et al., J. Exp. Med., 2001, 193:471). These experiments indicated that IL-6/sIL-6R mediated STAT3 activation plays a key role in the development and perpetuation of colitis. In another inflammatory model, rheumatoid arthritis (RA), STAT3 was shown to be important for the survival of RA synovial fibroblasts (Krause et al., J. Immunol, 2002, 169:6610). It was therefore suggested that STAT3 may be a good target for gene therapy. Constitutive STAT3 activation is also known to be a "cancer-causing" factor and is accompanied with the upregulation of anti-apoptotic proteins such as Bcl-2 and Bcl-XL (Turkson et al., Oncogene, 2000, 19:6613).

It was found that IL-6/sIL-6R mediated STAT3 activation was significantly reduced by sgp130(D1-3)Fc at efficacy levels which were comparable to the parental sgp130Fc compound. Moreover, sgp130(D1-3)Fc (sgp130Var) was expressed at higher amounts in eukaryotic cells than sgp130Fc, generated less undesired side products and was separable from remaining impurities by standard column chromatography. These advantages will significantly enhance the development of suitable GMP production procedures and will lower the costs of goods.

The expression of sgp130(D1-D3)S$_n$ is exemplarily shown for sgp130(D1-D3)S$_1$-Fc. A respective construct (pDEST40_sgp130(D1-D3)S$_1$-Fc) was transiently transfected into CHO cells. In parallel, another set of CHO cells was transfected with a construct comprising the parental sgp130Fc. The cells were incubated for 24 h, the supernatants were collected, and the sgp130 fusion proteins were immunoprecipitated. The precipitates were finally analyzed by SDS-PAGE and detected by using an anti-human IgG antibody according to standard Western blot procedures.

Figure 3:
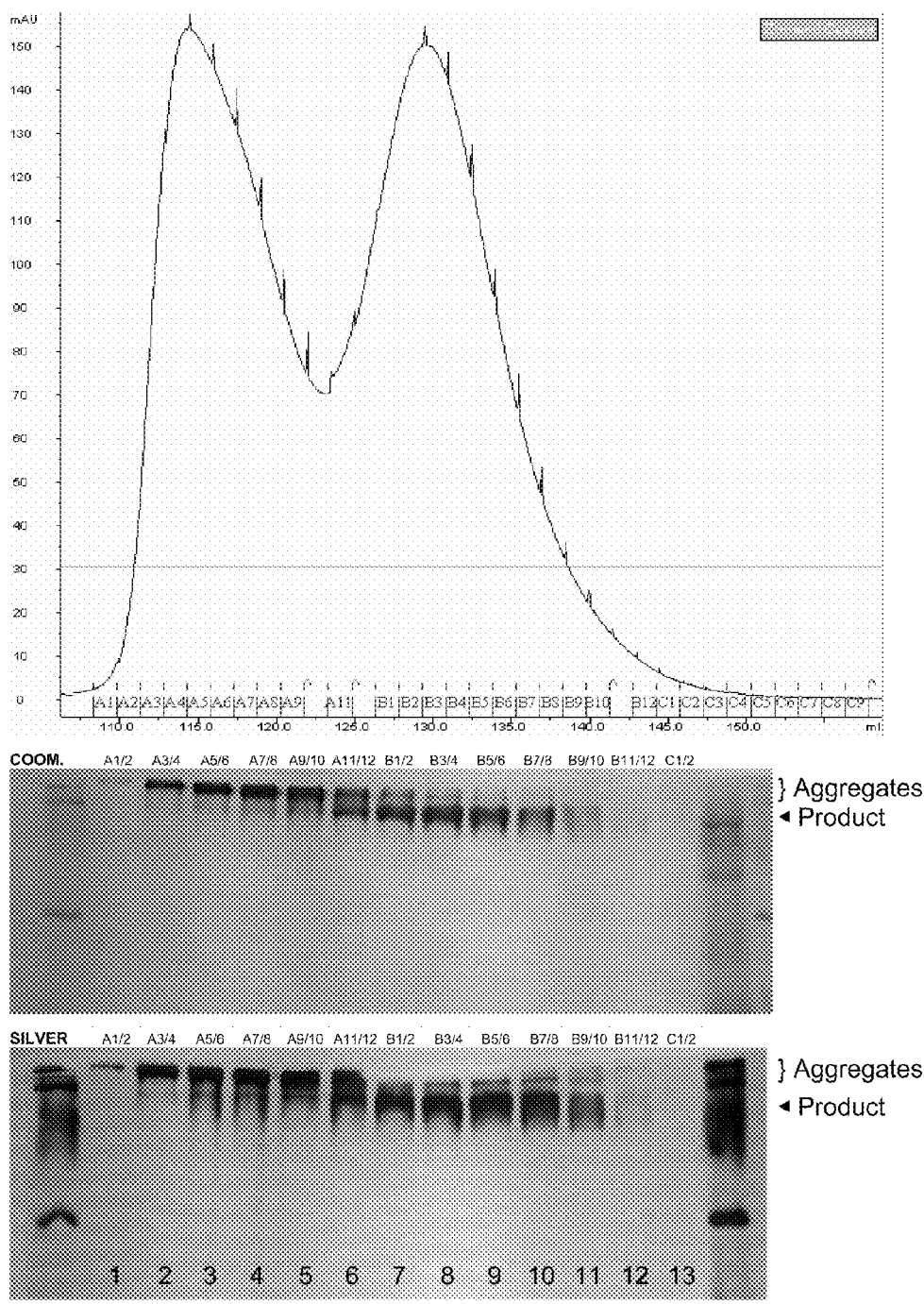

FIG. 3: Purification of sgp130Fc fusion molecules

Size exclusion chromatography (SEC) of sgp130Fc. The upper panel shows the elution profile (chromatogram) derived during gel filtration by UV scanning. The middle and lower panels represent the analysis of the collected fractions by native polyacrylamide gel electrophoresis (PAGE) and staining with either coomassie (COOM) or silver according to standard procedures.

Figure 4:
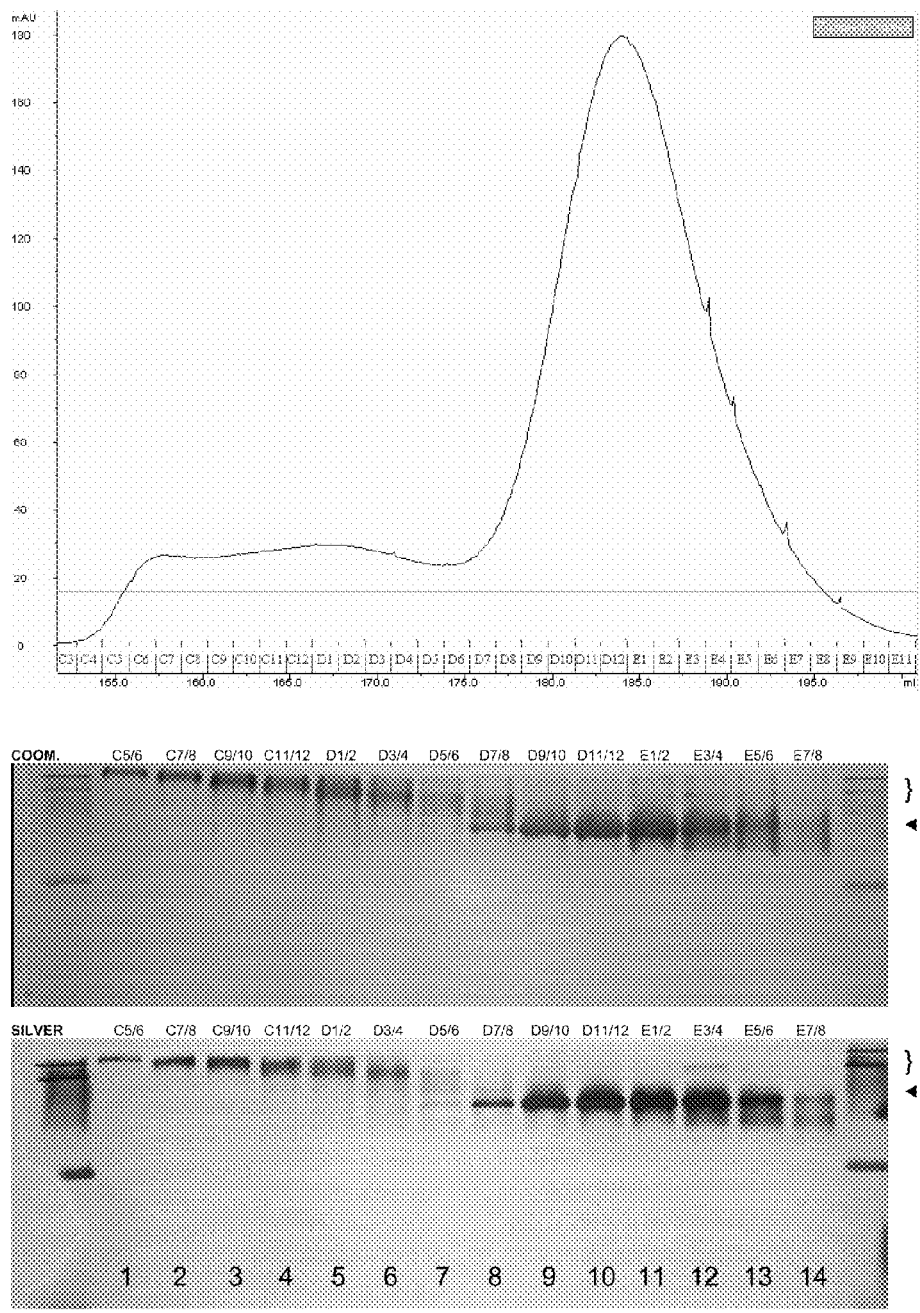

FIG. 4: Purification of sgp130(D1-D3)S$_n$-Fc fusion molecules (A) The purification of sgp130(D1-D3)S$_n$-Fc molecules by size exclusion chromatography (SEC) is exemplarily shown for sgp130(D1-D3)S$_1$-Fc. The upper panel shows the elution profile (chromatogram) derived during gel filtration by UV scanning. The middle and lower panels represent the analysis of the collected fractions by native polyacrylamide gel electrophoresis (PAGE) and staining with either coomassie (COOM) or silver according to standard procedures.

(B) A comparison of the SEC elution chromatograms of variants with (GGGGS)$_n$ spacers shows optimal purification properties with a spacer length of n=3 which does not correlate with a continuous increase in biological activity (see diagram below and FIG. 5)

Figure 5:
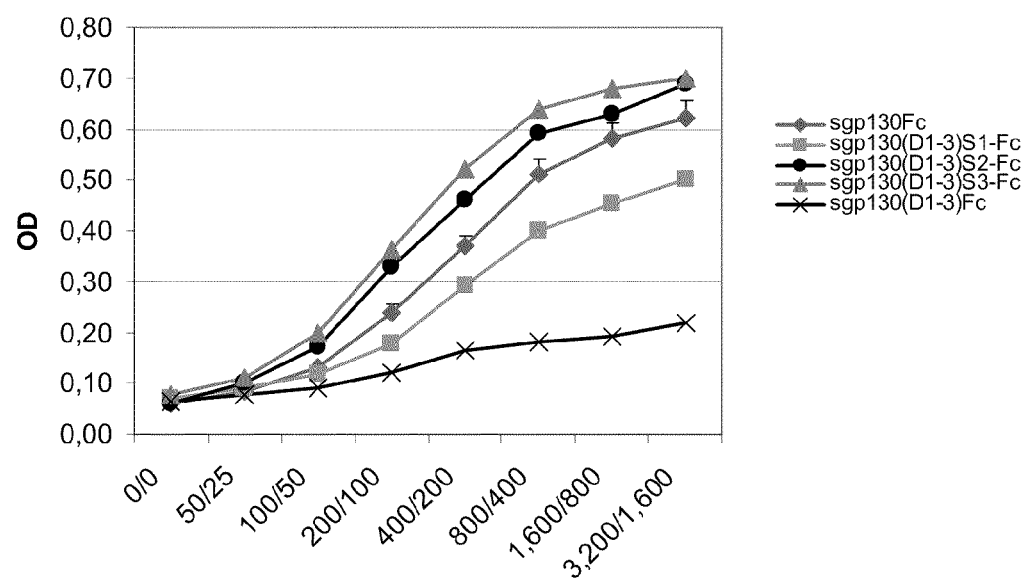

FIG. 5: Specific binding of IL-6/sIL-6R complexes by sgp130(D1-D3)S$_n$-Fc molecules Purified sgp130(D1-D3)S$_n$-Fc molecules (with n=0 to 3) were coated on 96-well plates and incubated with increasing amounts of recombinant IL-6+soluble IL-6 receptor (sIL-6R). Bound IL-6/sIL-6 complexes were detected using a mouse anti-IL-6R antibody and a horseradish peroxidase conjugated anti-mouse IgG antibody (□, ●, ■, ▲). In parallel the parental sgp130Fc molecule was tested (♦)

Figure 6:
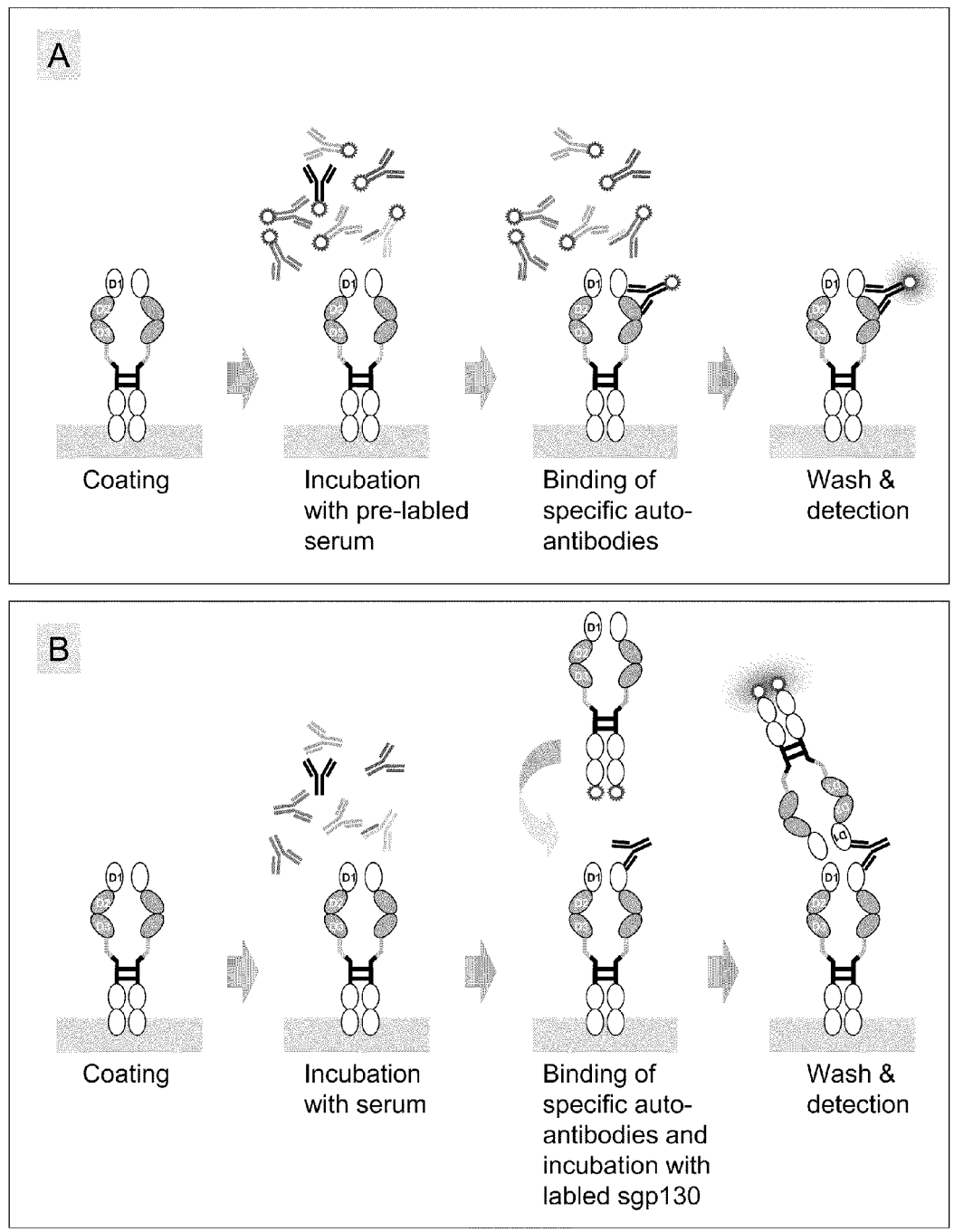

FIG. 6: Schematic drawing of an assay to detect sgp130 (D1-D3)S$_n$-Fc binding antibodies (A) sgp130(D1-D3)S$_n$-Fc fixed to a solid matrix is incubated with an antibody mixture (e.g. contained in serum samples) which was previously labeled (e.g. by fluorescence dyes). Unbound antibodies are washed away and specific binding molecules are detected by state-of-the-art technologies. (B) sgp130(D1-D3)S$_n$-Fc fixed to a solid matrix is incubated with an antibody mixture (e.g. contained in serum samples). Unbound antibodies are washed away and the remaining sgp130(D1-D3)S$_n$-Fc/antibody complex are subsequently incubated with a certain amount of labeled sgp130 (D1-D3)S$_n$-Fc (e.g. fluorescence dyes) and are finally detected by state-of-the-art technologies.

FIG. 7: cDNA sequence of optimized sgp130(D1-D3)

The sequence (SEQ ID NO: 3) includes the signaling peptide as well as the domains D1 to D3 of sgp130. The sequence was codon optimized for the expression of the encoded polypeptide in mammalian cells.

FIG. 8: Amino acid sequence of soluble gp130(D1-D3)

The polypeptide sequence depicted in FIG. 8 is SEQ ID NO: 4. Certain molecule fragments are underlined as follows: Signaling peptide () Ig-like C2 type domain (D1) (_ _ _); Fibronectin Type III domain (D2) (); Fibronectin Type III domain Domain (D3) (_ _).

Thus, the present invention relates to a polypeptide-dimer of two monomeric fragments, wherein the monomeric fragments comprise domains 1 to 3 (D1 to D3) of the extracellular part of glycoprotein (gp)130 and at their C-terminal ends a polypeptide spacer having a length of 5 to 30 amino acids, wherein both monomeric fragments are covalently linked to each other, wherein the spacer length determines optimal binding of the resulting dimeric protein to the IL-6/soluble IL-6 receptor complex and wherein said polypeptide-dimer exhibits a significantly reduced potential to build homomeric aggregates and molecule fragments, and wherein significantly higher productivity in host cells is obtained.

The polypeptide-dimers of the present invention may be engineered using known methods. The term "soluble" as used herein (abbreviation "s") refers to a gp130 molecule lacking at least the intracellular domain and the transmembrane domain. The domains utilised may consist of the extracellular domains D1 to D3 of gp130 or they may consist of mutants or fragments thereof that maintain the ability to inhibit the activity of the agonistic complex IL-6/sIL-6R. Preferably, the polypeptide corresponding to the soluble part of gp130 is the only biologically active polypeptide of the polypeptide-dimer of the present invention.

In a preferred embodiment, the two monomeric fragments of the polypeptide-dimer of the present invention are identical.

In an even more preferred embodiment of the polypeptide-dimer of the present invention, the dimer does not contain further domains (D4 to D6) of sgp130.

The linkage of two monomers to build the dimer can be carried out by a person skilled in the art by well known methods. In order to form the dimer the two soluble gp130 molecules can be linked to each other via one or more disulfide bridges. This can be achieved, e.g. by recombinant expression, wherein the nucleic acid sequence encoding sgp130 is fused at its C-terminus to a polypeptide linker which contains one or more codons encoding cysteine residues between the C-terminus of sgp130 and the stop-codon. Alternatively, for generating the dimer one may employ linkers to the end of each sgp130 molecule which confer any other kind of intermolecular binding (e.g. covalent, ionic) between the two sgp130 molecules. This linkers may by entirely artificial (e.g., polyglycine repeats which may be interrupted by serine, alanine and/or threonine at a certain interval). Alternatively, for generating the dimer the two soluble gp130 molecules may be C-terminal fused to an IgG-Fc fragment including hinge region (either directly or via a linker). In addition free cysteine residues within the hinge region of the Fc molecule may be deleted by mutation to reduce the risk of building undesired intermolecular disulfide bridges. Additionally, the molecules of the dimer may be tagged, e.g. by His-His-His-His-His-His (His6, SEQ ID NO: 1), Myc, Strep, polyarginine, Flag, green fluorescence protein (GFP), TAP, glutathione S-transferase (GST), HA, calmodulin-binding peptide (CBP), maltose-binding protein (MBP), V5, HSV, S, vesicular stomatitis virus (VSV), Protein C, Luciferase, Glu-Glu, E, beta-GAL, T7 or other epitopes to which antibodies or other binding molecules are available to allow purification by suitable chromatography systems and/or detection, e.g. by western blot, ELISA, bioassays etc.

In order to confer an optimal distance between the two sgp130 subunits within the dimeric molecule which is necessary to obtain optimal binding to the IL-6/sIL-6R complex, the sgp130 subunits are fused at their C-terminal end to (poly) peptide spacers having a length of 5 to 30 amino acids, preferably (i) 10 to 25 or (ii) 15 to 25 amino acids or, particularly preferred, 10 to 15 amino acids. The kind of amino acids building the spacer is not particularly critical, however, amino acids (like G or S) are preferred which (a) ensure ideal steric flexibility allowing an optimum alignment of the monomers, (b) are not easily accessible by proteases and antibodies and (c) are not charged in order to reduce or eliminate any undesired aggregation of the dimer with other molecules or the formation of trimers, etc. Preferred amino acids for building the spacer molecule are one or more repeats of the amino acid sequence "GGGGS" (SEQ ID NO: 2) but the spacer can comprise any other sequence which enhances ligand binding of said sgp130 molecule.

In particularly preferred embodiment of the polypeptide-dimer of the present invention, the spacer is selectively glycosylated to protect the molecule from proteolytic cleavage.

In a further particularly preferred embodiment, the polypeptide-dimer of the present invention forms less than 50% of homomeric aggregates and molecule fragments, preferably less than 25% of homomeric aggregates and molecule fragments, more preferably less than 10% of homomeric aggregates and molecule fragments and, most preferably, less than 5% of homomeric aggregates and molecule fragments.

The present invention also provides polynucleotides encoding a polypeptide-dimer (or the respective monomers) of the present invention, which can be codon optimized for the efficient production of the encoded protein in eukaryotic host cells, bacteria, yeast or insect cells. Preferably, said polynucleotide comprises the nucleic acid sequence shown in FIG. 7.

Furthermore, the present invention also relates to expression vectors containing a polynucleotide of the invention and corresponding host cells.

A variety of means can be used to generate and identify mutations or modifications of sgp130 that have the desired properties. Site-directed mutagenesis by standard techniques of the DNA encoding sgp130 or state-of-the-art methods such as restriction digest and ligation may be used, followed by analysis of the collection of products to identify mutated molecules having the desired properties.

The polypeptide-dimers of the present invention are preferably recombinantly produced by use of polynucleotides encoding a polypeptide of the present invention and vectors, preferably expression vectors containing said polynucleotides. For the production of the polypeptides of the invention, the polynucleotides are obtained from existing clones, i.e. preferably encode the naturally occurring polypeptide or a part thereof. Polypeptides encoded by any polynucleotide which hybridizes to the complement of the native DNA or RNA under highly stringent or moderate stringent conditions (for definitions, see Sambrook, Molecular Cloning A Laboratory Manual, Cold Spring Harbor Laboratory (1989) N.Y.) as long as that polypeptide maintains the biological activity of the native sequence, are also useful for producing the polypeptide(s) of the present invention.

The recombinant vectors can be constructed according to methods well known to the person skilled in the art, e.g., Sambrook, Molecular Cloning A Laboratory Manual, Cold Spring Harbor Laboratory (1989) N.Y. A variety of expression vector/host systems may be utilized to contain and express sequences encoding the sgp130 polypeptides of the present invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g. baculovirus); plant cell systems transformed with virus expression vectors (e.g., cauliflower mosaic virus, CaMV, tobacco mosaic virus, TMV) or bacterial expression vectors (e.g. Ii or pBR322); or animal cell systems.

The "control elements" or "regulatory sequences" are those non-translated regions of the vector-enhancers, promoters, 5'- and 3'-untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSPORT1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding the sgp130 polypeptides, vectors based on SV40 or EBV may be used with an appropriate selectable marker.

In bacterial systems, a number of expression vectors may be selected depending upon the use intended for the polypeptide dimer of the present invention. Vectors suitable for use in the present invention include, but are not limited to the pSKK expression vector for expression in bacteria.

In the yeast, *Saccharomyces cerevisiae*, a number of vectors containing constitutive or inducible promoters such as alpha factor, alcohol oxidase, and PGH may be used; for reviews, see Grant et al. (1987) Methods Enzymol. 153:516-544.

In cases where plant expression vectors are used, the expression of sequences encoding the antibody of the present invention may be driven by any of a number of promoters. For example, viral promoters such as the 35S and 19S promoters of CaMV may be used alone or in combination with the omega leader sequence from TMV (Takamatsu, N (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). The constructs can be introduced into plant cells by direct DNA transformation or pathogen-mediated transfection. Such techniques are described in a number of generally available reviews (see, for example Hobbs, S, and Murry, L. E. in McGraw Hill Yearbook of Science and Technology (1992) McGraw Hill, New York, N.Y.; pp. 191-196.

An insect system may also be used to express the sgp130 molecules of the present invention. For example, in one such system, *Autographa california* nuclear polyhedrosis virus (AcNPV) is used as a vector to express foreign genes in *Spodoptera frugiperda* cells or in *Trichoplusia* larvae. The sequences may be cloned into a non-essential region of the virus, such as the polyhedrin gene, and placed under control of the polyhedrin promoter. Successful insertion of the gene encoding sgp130 will render the polyhedrin gene inactive and produce recombinant virus lacking coat protein. The recombinant viruses may then be used to infect, for example *S. frugiperda* cells or *Trichoplusia larvae* in which APOP may be expressed (Engelhard, E. K. et al. (1994) Proc. Nat. Acad. Sci. 91:3224-3227).

In mammalian host cells, a number of viral-based expression systems may be utilized. In cases where an adenovirus is used as an expression vector, sequences encoding the polypeptide(s) of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the protein in infected cells (Logan, J. and Shenk, T. (1984) Proc. Natl. Acad. Sci. 81: 3655-3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation. Such signals include the ATG initiation codon and adjacent sequences. In cases where sequences encoding the sgp130, its initiation codon, and upstream sequences are inserted into the appropriate expression vector, no additional transcriptional or translational control signals may be needed. However, in case where only coding sequence is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed polypeptide chains in the desired fashion. Post-translational processing which cleaves a "prepro" form of the polypeptide may also be used to facilitate correct insertion, folding and/or function. Different host cells which have specific cellular machinery and characteristic mechanisms for post-translational activities (e.g., CHO, HeLa, MDCK, HEK293, or W138), are available from the American Type Culture Collection (ATCC; Bethesda, Md.) and may be chosen to ensure the correct modification and processing of the foreign polypeptide chains.

For long-term, high-yield production of recombinant polypeptides, stable expression is preferred. For example, cell lines which stably express sgp130 chains may be transformed using expression vectors which may contain viral origins of replication and/or endogenous expression elements and a selectable marker gene on the same or on a separate vector. Following the introduction of the vector, cells may be allowed to grow for 1-2 days in an enriched medium before they are switched to selective media. The purpose of the selectable marker is to confer resistance to selection, and its presence allows growth and recovery of cells which successfully express the introduced sequences. Resistant clones of stable transformed cells may be proliferated using techniques appropriate to the cell type.

After the introduction of the recombinant vector(s), the host cells are grown in a selective medium, which selects for growth of vector-containing cells. Any number of selection systems may be used to recover transformed cell lines. These include, but are not limited to, the herpes simplex virus thymidine kinase (Wigler, M. et al. (1977) Cell 11:223-232) and adenine phosphoribosyltransferase (Lowy, I. et al. (1980) Cell 22:817-823) genes which can be employed in tk.sup. or aprt.sup.-cells, respectively. Also, antimetabolite, antibiotic or herbicide resistance can be used as the basis for selection; for example, dhfr which confers resistance to methotrexate (Wigler, M. et al. (1980) Proc. Natl. Acd. Sci. 77:3567-3570); npt, which confers resistance to the aminoglycosides neomycin and G-418 (Colbere-Garapin, F. et al. (1981) J. Mol. Biol. 150:1-14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and Mulligan, R. C. (1988) Proc. Natl. Acad. Sci. 85:8047-8051). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Purification of the recombinant polypeptides is carried out by any one of the methods known for this purpose, i.e., any conventional procedure involving extraction, precipitation, chromatography, electrophoresis, or the like. A further purification procedure that may be used is affinity chromatography using monoclonal antibodies or other molecules which bind the target polypeptide and which are produced and immobilized on a gel matrix contained within a column. Impure preparations containing the recombinant polypeptide are passed through the column or the matrix will be used in a batch technology to bind target polypeptides. The polypeptide will be bound to the matrix while the impurities will not. After washing the polypeptide is eluted from the matrix by a change in pH or ionic strength.

Accordingly, the present invention also relates to a method of producing the polypeptide-dimer of the present invention, comprising culturing a host cell transformed with a DNA sequence encoding said polypeptide and recovering the polypeptide from said host cell or the culture medium.

The polypeptide-dimers of the present invention are useful in the treatment and/or prevention of all pathologies, in which the activity of the agonistic IL-6/sIL-6R complex contributes to the pathogenesis of a disease and must be inhibited. For example, therapeutic uses of the polypeptide-dimers of the present invention would include the following:

a) IL-6 appears to be directly involved in multiple myeloma by acting in either an autocrine or paracrine fashion to promote tumor formation. Furthermore, the elevated IL-6 levels create undesirable secondary effects such as bone resorption, hypercalcemia and cachexia. In these cases it is known that sIL-6R sensitizes target cells for IL-6. Therefore, the polypeptide-dimers of the invention as described herein would be beneficial for both the secondary effects as well as inhibiting tumor growth.

b) In autoimmune diseases: the pathogenic significance of IL-6 in autoimmune disorders has been reviewed by many authors in the literature (see, e.g. Yoshizaki et al. (1992) Semin. Immunol. 4(3):155-166), thus, interference with IL-6 signal transduction may be useful for autoimmune disease therapy (Nishimoto et al. (1999) Intern. Med. 38(2):178-182). Examples of such pathologies are systemic lupus erythematosus, Hashimoto's thyroiditis, scleroderma, rheumatoid arthritis, multiple sclerosis, autoimmune epithelitis, diabetes mellitus, Sjögren's syndrome, polymyositis, glomerulonephritis and other inflammatory diseases, such as psoriasis, Crohn's disease, ulcerative colitis and uveitis. Furthermore, certain inflammation-associated cancer diseases such as colon cancer are mentioned.

c) In osteoporosis, which can be exacerbated by lowering of estrogen levels in postmenopausal women or through ovariectomy, IL-6 appears to be critical mediator of osteoclastogenesis, leading to bone resorption. Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts. While estrogen replacement therapy is also used, there appear to be side effects that may include an increased risk of endometrial and breast cancer. Thus, the polypeptide-dimers of the present invention would be more specific to reduce osteoclastogenesis to normal levels.

d) IL-6 may be a mediator of tumor necrosis factor (TNF) that leads to cachexia associated with AIDS and cancer, perhaps by reducing lipoprotein lipase activity in adipose tissue. Accordingly, the polypeptide-dimers of the invention described herein would be useful in alleviating or reducing cachexia in such patients.

e) Bacterial and viral infections: the presence of Human Herpes Virus (HHV8) has been demonstrated in more than 91% of Karposi's sarcoma (KS) lesions. Moreover, the virus has been identified in primary effusion lymphoma (PEL) and in patients with multicentric Castleman's disease (MCD). Intriguingly, bone marrow dendritic cells from multiple myeloma (MM) patients were shown to be infected by HHV8. Since then, the association of HHV8 with MM has been a subject of fierce debate, which was recently revived. The genome of HHV8 codes for several proteins with significant homologies to human anti-apoptotic proteins, chemokines, and cytokines including a vital form of viral IL-6 (vIL-6) with 25% homology to human IL-6. vIL-6 has been demonstrated to have biologic activities reminiscent of human IL-6, i.e. stimulation of proliferation of murine hybridoma and human myeloma cells. More recently it was shown in mice injected with vIL-6-transfected NIH3T3 cells, that vIL-6 induced angiogenesis and hematopoiesis. It was concluded that through these functions vIL-6 played an important role in the pathogenesis of HHV8-associated disorders. The contribution of the IL-6R to vIL-6 signaling has been discussed controversially. One group using unpurified supernatants of vIL-6 transfected COS-7 cells has shown that STAT activity was induced in cells expressing gp130 but no IL-6R. In contrast, another group found that the activity of vIL-6 was reduced by an IL-6R antagonist, arguing for an involvement of IL-6R in vIL-6 signaling.

Thus, the present invention also relates to a pharmaceutical composition containing an effective amount of a polypeptide-dimer or polynucleotide of the present invention, preferably combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

An "effective amount" refers to an amount of the active ingredient that is sufficient to affect the course and the severity of the disease, leading to the reduction or remission of such pathology.

An "effective dose" useful for treating and/or preventing these diseases or disorders may be determined using methods known to one skilled in the art (see for example, Finl et al. (1975) The Pharmacological Basis of Therapeutics, Goodman and Gilman, eds. Macmillan Publishing Co., New York, pp. 1-46).

Administration of suitable compositions may be effected by different way, e.g. by intravenous, intraperitoneal, subcutaneous, intramuscular, topical (e.g. enema, inhalation, salve, drops) or intradermal administration. The route of administration, of course, depends on the kind of therapy and the kind of compound contained in the pharmaceutical composition. The dosage regimen will be determined by the attending physician and other clinical factors. As is known in the medical arts, dosages for any one patient depends on many factors, including the patients size, body surface area, weight, age, sex, the particular compound to be administered, time and route of administration, the kind of therapy, general health and other drugs being administered concurrently.

Preferred medical uses of the polypeptide-dimers and polynucleotides of the present invention described above are the treatment of bone resorption, hypercalcemia, cachexia, tumors, cancer, autoimmune diseases, inflammatory diseases such as Crohn's disease, ulcerative colitis, rheumatoid arthritis, juvenile rheumatoid arthritis, asthma, psoriasis, lupus erythematosus, multiple sclerosis, uveitis and others, bacterial or viral infections.

Finally, the present invention also relates to antibodies binding to a polypeptide-dimer of the invention. Preferably, said antibodies bind to the spacer region, the linker region and/or the D3/spacer junction region. Said antibodies are useful in a diagnostic method which is based on the detection of said antibodies which are bound to a polypeptide-dimer of the invention.

The below examples explain the invention in more detail:

EXAMPLE 1

Preparation of the sgp130 Variants
sgp130(D1-D3)$S_n$-Fc (A) Material

The codon optimized sequence of sgp130Fc (full length) was synthesized and provided as a pCR-Script-AMP construct by GeneART (Regensburg, Germany). The Gateway cloning system components (AccuPrime Pfx DNA Polymerase, the donor vector pDONR221, the CMV promoter-controlled expression vector pcDNA-DEST40, BP and LR recombinase for insert transfer and competent E. coli cells) were purchased from Invitrogen (Karlsruhe, Germany). The QuikChange II site-directed mutagenesis kit was obtained from Stratagene (Amsterdam, The Netherlands). HYPUR purified mutagenesis primers were from MWG Biotech (Ebersberg, Germany). CHO-K1 cells were obtained from the German Collection of Microorganisms and Cell Cultures (Braunschweig, Germany). Culture medium components were purchased as follows: Ham's F12 medium and PBS (PAA Laboratories; Cölbe, Germany), FBS (Biochrom; Berlin, Germany), Trypsin/EDTA solution (Invitrogen) and G418 solution (Sigma-Aldrich; Taufkirchen, Germany). The transfection reagent Lipofectamine 2000 was from Invitrogen. Santa Cruz (Heidelberg, Germany) supplied Protein A/G Plus Agarose for immunoprecipitation. For both immunoprecipitation and primary detection in Western blots, a mouse anti-human IgG (Fc) monoclonal antibody was used (CBL102; Chemicon; Hofheim, Germany). Western blot secondary detection was performed with a anti-mouse IgG HRP-linked antibody, ECL-Plus Western blotting substrate and Hyperfilm ECL (all from GE Healthcare; Freiburg, Germany). Roller bottles (2.1 L, 2.5× surface) were purchased from Greiner Bio-One (Frickenhausen, Germany).

(B) Construction of sgp130(D1-D3)$S_n$-Fc

The full-length sgp130Fc was subcloned into pDONR221 using Gateway primers, AccuPrime Pfx DNA Polymerase and BP recombinase in a standard Gateway procedure. The subcloned insert was completely sequence-verified using stacked forward and reverse sequencing primers every 250-300 bp. In a site-directed mutagenesis with the QuikChange II kit, the domains D4-D6 of sgp130Fc were replaced by ideal spacer elements (S1, S2, S3 and S5) using a primer pair which bridged the end of domain D3 (YED) and the beginning of the Fc part (SCD) of sgp130Fc and encoded a different number of repeats of the amino acid spacer sequence "glycine-glycine-glycine-glycine-serine" (GGGGS, SEQ ID NO: 2). The variant sgp130(D1-D3)Fc was left without spacer (for clarification purposes: if a variant "sgp130(D1-D3)S0-Fc" is mentioned this means that the molecule does not contain a spacer peptide and therefore is identical to sgp130(D1-D3) Fc). Positive clones were identified by restriction digest with AlwNI and verified by complete sequencing as described above. Subsequently, the insert was transferred to the expression vector pcDNA-DEST40 by Gateway LR recombination. As the insert encodes two stop codons after the Fc part, the tags of pcDNA-DEST40 (V5 and 6×His epitopes) are not present in the proteins sgp130(D1-D3)Sn-Fc. Again, positive clones were identified by AlwNI restriction digest. A sequence verification was not necessary, as the Gateway recombination procedure is highly specific and does not involve DNA amplification. The correct transfer of inserts using Gateway recombinases has been verified in independent experiments in our laboratory.

(C) Culture and Transfection

CHO-K1 cells were grown in Ham's F12 medium supplemented with 10% FBS at 37° C. and 5% $CO_2$ in a water-saturated atmosphere. Maintenance cultures were split every 3-4 days and used only up to 20 passages. Cells were transfected with the expression construct pcDNA-DEST40_sgp130(D1-D3)$S_n$-Fc using Lipofectamine 2000 and standard conditions for CHO-K1 supplied by Invitrogen. For a first transient expression test, CHO-K1 were transfected in 6-well plates, and both cells and supernatants were harvested 24 h after transfection. sgp130(D1-D3)$S_n$-Fc was immunoprecipitated from the supernatants using Protein A/G Plus Agarose and the anti-human IgG (Fc) antibody according to the manufacturer's instructions. Whole cell protein was extracted and Western blots with anti-human IgG (Fc) antibody were performed with the cell lysates and immunoprecipitates as described in Waetzig et al., J. Immunol. 168: 5342 (2002).

(D) Expression of sgp130(D1-D3)$S_n$-Fc in CHO Cells

After successful transient expression, CHO-K1 cells were transfected and selected using 400 μg/ml G418 in 10-cm plates. For a first impression of product quality and properties, a pre-selected polyclonal CHO-K1 pool was transferred to roller bottles. Supernatants of the confluent cells were harvested three times a week, centrifuged twice at 4,000 rpm and 4° C. for 15 min to remove cell debris and either processed immediately or frozen at −80° C. In parallel, stable cell clones were selected from a pre-selected pool using the limited dilution method and characterized by Western blot expression analysis as described above. The clone with the highest and most stable expression was transferred to roller bottles and used for further production.

(E) Results

Figure 1:
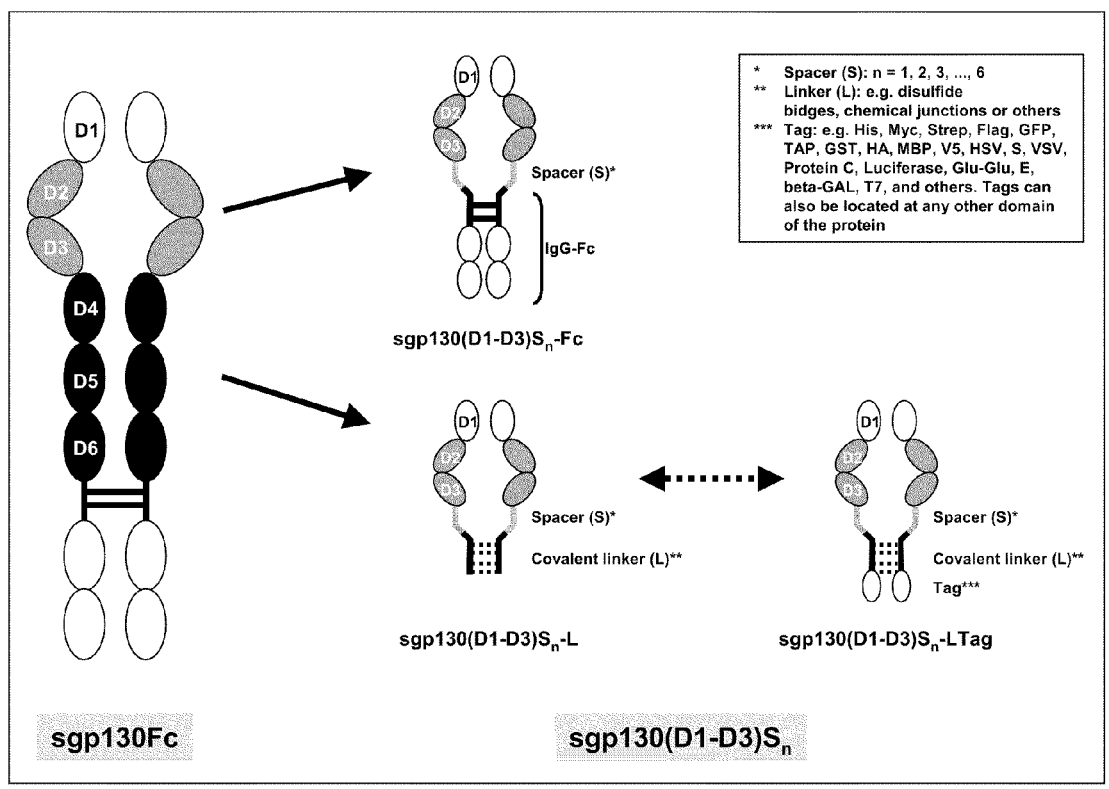
FIG. 1: Schematic drawing of sgp130(D1-D3)S$_n$ molecules sgp130(D1-D3)S$_n$ variants are generated by deletion of the domains D4 to D6 of the parental molecule sgp130Fc and their replacement by a polypeptide spacer of various length (S$_n$). "n" indicates the number of repeats within the spacer region. Subsequently the molecule is covalently dimerized either by an IgG-Fc fragment (upper panel) to build sgp130 (D1-D3)S$_n$-Fc or (lower panel) by further fusion to a naturally occurring or artificial linker element which confers covalent junctions, e.g. by formation of disulfide bridges, chemical interactions, or others (sgp130(D1-D3)S$_n$-L). In addition, these molecules can contain sequence tags for purification and/or detection purposes.
Figure 2:
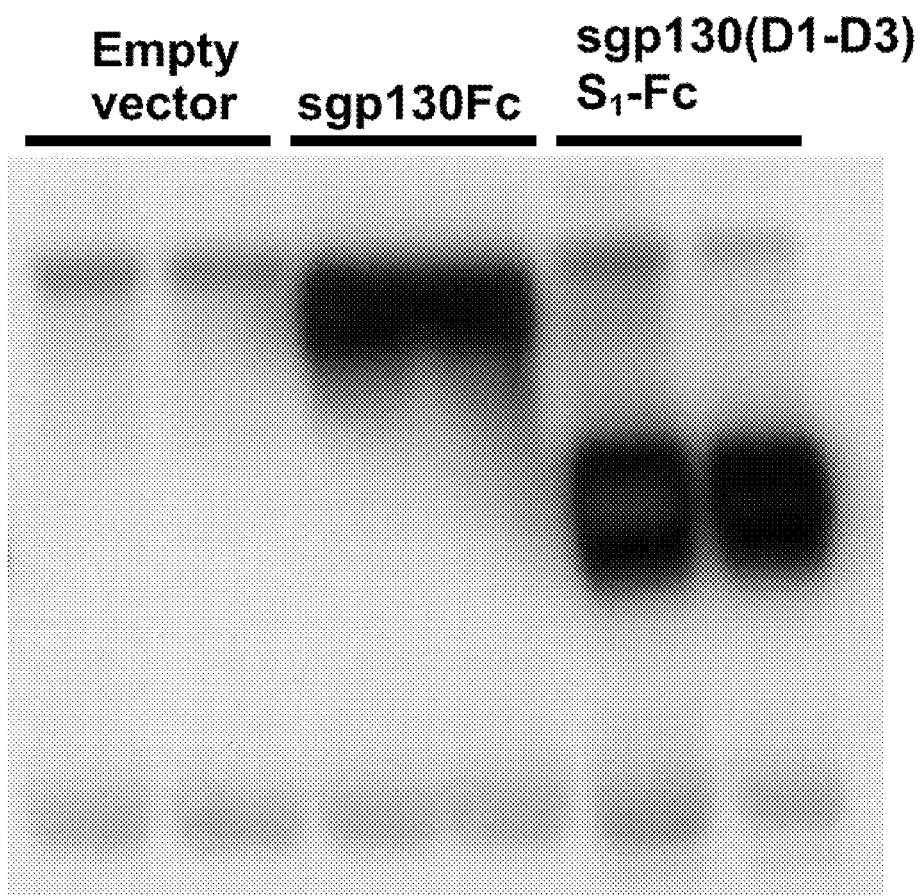
FIG. 2: Expression of sgp130(D1-D3)S$_n$ in CHO cells

As demonstrated in FIG. 2, sgp130(D1-D3)$S_n$-Fc (exemplarily shown for sgp130(D1-D3)$S_1$-Fc) was expressed at production rates which were even better than those obtained for the parental sgp130Fc protein. This indicates that the expression of a smaller variant of sgp130Fc appears to be enhanced and confers advantages for the preparation of the protein. Finally, higher production rates will significantly lower the costs for the industrial production.

EXAMPLE 2

Purification of sgp130(D1-D3)$S_n$-Fc (A) Material

Cellulose acetate filters (0.45 μm) for a vacuum filter unit were purchased from Sartorius (Göttingen, Germany). PBS was from PAA Laboratories (Cölbe, Germany). Materials for affinity and size exclusion chromatography (SEC) were all obtained from GE Healthcare (Freiburg, Germany): MabSelect material (product code 17-5199-01) in a XK16/20 column, PD-10 desalting columns and HiLoad 26/60 Superdex 200 pg for SEC. Amicon Ultra-15 50 kD Ultracel-PL membrane concentration units were purchased from Millipore (Eschborn, Germany). Ready-made acrylamide-bis solution (19:1, 30%) for PAGE was supplied by Bio-Rad (Munich, Germany).

(B) Affinity Chromatography

The purification of the sgp130(D1-D3)$S_n$-Fc variants is exemplarily shown for sgp130(D1-D3)$S_1$-Fc. sgp130(D1-D3)$S_1$-Fc-containing supernatants from roller bottle cultures were purified at 4° C. using a P-1 peristaltic pump and a ÄKTA Purifier 100 System (both from GE Healthcare; Freiburg, Germany). The protocol was based on the manufacturer's recommendations for the purification of monoclonal antibodies. After centrifugation, the pH of the fresh or thawed (on ice) supernatant was adjusted to 6.7-7.0. After two rounds of vacuum filtration (0.45 μm), the supernatant was degassed and—if necessary—pH was adjusted again to a value of 6.7-7.0. Subsequently, the PBS-equilibrated affinity chromatography column (6-25 ml MabSelect in a XK16/20 column) was loaded with 2-4 L of supernatant at a flow rate of 3-10 ml/min using the P-1 pump. After washing with PBS, the column was transferred to the ÄKTA purifier and washed again with PBS until the $A_{280}$ stabilized after quantitative removal of unbound protein. For the elution, the ÄKTA system was equipped with two 50 mM sodium citrate buffers at pH 3.25 and 5.5, respectively, which were mixed to produce the desired pH conditions. One washing step at pH 5.1 was followed by elution with pH 3.7. Fractions of 10 ml were collected in 15-ml tubes containing 2 ml 1 M Tris-HCl (pH 11). The peak fractions were pooled, and the pH was measured and adjusted to 7.5, if necessary. Pool protein concentration was measured by $A_{280}$ and the pool was carefully concentrated to a maximum of 1.5 mg/ml using Amicon Ultra-15 50 kD units. PBS-equilibrated PD-10 desalting columns were used to change the buffer to PBS, followed by another protein concentration measurement at 280 nm.

(C) Size Exclusion Chromatography (SEC) by Gel Filtration

For SEC, a maximum concentration of 1.2 mg/ml in PBS was recommendable. SEC was performed with the ÄKTA system in a PBS-equilibrated HiLoad 26/60 Superdex 200 pg column at a flow rate of 0.8 ml/min. sgp130(D1-D3)$S_1$-Fc eluted in a single peak after a low plateau of aggregates of higher molecular weight (FIG. 4A). In the first runs, samples of all fractions were obtained for PAGE analysis (see below). Peak fractions were pooled, their protein concentrations were measured and set to 400-500 µg/ml in PBS, and single-use aliquots were frozen at −80° C. for long-term storage.

(D) Polyacrylamide Gel Electrophoresis (PAGE)

Fraction and pool samples were analysed by native PAGE (7.5% polyacrylamide gel) and subsequent silver or Coomassie staining (FIG. 4A).

(E) Results

As shown in FIGS. 4A and 4B, the amount of undesired side product is significantly reduced as compared to the parental compound sgp130Fc which was in parallel purified in another experiment (results are shown in FIG. 3). Moreover, the elution of the main product (lane 8 to 14 in FIG. 4A) is clearly separable from the impurity fractions (lanes 1 to 6 in FIG. 4A). sgp130Fc tends to generate much higher amounts of impurities (see first chromatogram peak and PAGE in FIG. 3). Moreover, none of the elution fractions containing the main product (lane 6 to 11 in FIG. 3) is free of impurities. These results indicate a clear improvement of sgp130(D1-D3)$S_n$-Fc in comparison to the parental sgp130Fc molecule. However, the spacer length is decisive for the purifiability of the sgp(130(D1-D3)$S_n$-Fc molecules. The binding activity and, thus, therapeutic efficacy improves with increasing length of the spacer. There is a "window of optimal purifiability" with an optimum at n=3 (FIG. 4B). Therefore, the ideal spacer length is between 3 and 5 elements, depending on the need of optimal activity or optimal purity and yield.

EXAMPLE 3

Comparison of the IL-6/sIL-6R Complex Binding Properties of sgp130Fc and sgp130(D1-D3)$S_n$-Fc (A) Material The 96-well Microlon microtiter plates were purchased from Greiner Bio-One (Frickenhausen, Germany). Recombinant human IL-6 and soluble IL-6 receptor (sIL-6R) were obtained from BioSource (Solingen, Germany) and R&D Systems (Wiesbaden, Germany), respectively. The primary anti-sIL-6R antibody (clone M91, mouse IgG1) was from Beckman Coulter (Krefeld, Germany). The secondary anti-mouse IgG HRP-conjugated antibody from GE Healthcare (Freiburg, Germany) was the same as in the Western blotting experiments (see Example 1, A and C). Ready-to-use Tetramethylbenzidin (TMB) HRP substrate was purchased from Sigma-Aldrich (Taufkirchen, Germany).

(B) Enzyme-Linked Immunosorbent Assay (ELISA)

For quality control and comparison between different lots of sgp130Fc variants, a standard ELISA was designed. All steps except for coating were carried out at room temperature, all washing steps were performed three times with a volume of 250 µl, and all conditions were measured in triplicate. A 96 well microtiter plate was coated with 100 ng/Well of original sgp130Fc as an internal standard and an equimolar quantity of sgp130(D1-D3)$S_n$-Fc in 100 µl PBS at 4° C. overnight. Thus, sgp130Fc and its variants served as capture reagent, while the bound sIL-6R was detected (see below). After washing with 0.05% Tween-20/PBS, wells were blocked with 200 µl/Well 3% BSA/PBS for 2 h. Subsequently, the blocking solution was removed, and wells were incubated for 1 h with a 1:2 dilution series (100 µl/Well) of recombinant human IL-6 (3.2 µg/ml to 50 ng/ml) and sIL-6R (1.6 µg/ml to 25 ng/ml) in 3% BSA/PBS. After washing with 0.05% Tween-20/PBS, wells were incubated with the primary anti-sIL-6R antibody diluted 1:2,000 in 3% BSA/PBS (100 µl/Well) for 1 h. Another series of three washing steps with 0.05% Tween-20/PBS was followed by a 1-h incubation with the secondary anti-mouse IgG HRP-conjugated antibody at 1:5,000 (100 µl/Well). After washing with 0.05% Tween-20/PBS and subsequently with dH$_2$O, plates were incubated with 100 µl/Well TMB substrate for about 5 min (depending on the intensity of the developing blue colour). The substrate reaction was stopped by adding 100 µl/Well 0.5 M sulfuric acid to the wells. Finally, the $A_{450}$ was measured in a microplate reader.

(C) Results

The results of the binding assay are shown in FIG. 5. The binding efficiency of sgp130(D1-D3)$S_n$-Fc was mainly dependent on the number of spacer repeats used in the respective variants. In this case the variants containing 2 and 3 repeats ($S_2$ and $S_3$) were binding equal or even better than sgp130Fc. This indicates that the modification of the parental sgp130Fc molecule to improve its purification did not influence its biological activities and its putative use as a medicament for the treatment of IL-6 triggered diseases.

The invention claimed is:

1. A polypeptide-dimer of two monomeric fragments, wherein each of the monomeric fragments comprises: (a) SEQ ID NO: 4, but does not contain domains 4 to 6 (D4 to D6) of the extracellular part of glycoprotein 130, and (b) a polypeptide spacer having a length of 5 to 30 amino acids at its terminal end, wherein both monomeric fragments are covalently linked to each other, and the spacer length determines an optimal binding of the resulting dimeric protein to the IL-6/soluble IL-6 receptor complex.

2. The polypeptide-dimer of claim 1, wherein the two monomeric fragments are identical.

3. The polypeptide-dimer of claim 1, wherein covalent dimerization of both monomers is obtained by one or more disulfide bridges.

4. The polypeptide-dimer of claim 3, wherein the disulfide bridge(s) are generated by fusing the monomeric fragments to an IgG-Fc molecule.

5. The polypeptide-dimer of claim 3, wherein the disulfide bridge(s) are generated by fusing the monomeric fragments to a naturally occurring or artificial polypeptide, which comprises one or more free accessible cysteine residues.

6. The polypeptide-dimer of claim 1, wherein the polypeptide spacer is selectively glycosylated to protect the molecule from proteolytic cleavage.

7. The polypeptide-dimer of claim 1, wherein the polypeptide spacer has a length of 10 to 25 amino acids.

8. The polypeptide-dimer of claim 7, wherein the polypeptide spacer has a length of 15 to 25 amino acids.

9. The polypeptide-dimer of claim 1, wherein the spacer has the amino acid sequence (GGGGS)$_n$ with n being 1, 2, 3, 4, 5 or 6.

10. The polypeptide-dimer of claim 1, which forms less than 50% of homomeric aggregates and molecule fragments.

11. The polypeptide-dimer of claim 10, which forms less than 25% of homomeric aggregates and molecule fragments and molecule fragments.

12. The polypeptide-dimer of claim 11, which forms less than 10% of homomeric aggregates and molecule fragments.

13. The polypeptide-dimer of claim 12, which forms less than 5% of homomeric aggregates and molecule fragments.

14. A polynucleotide encoding a monomeric fragment of claim 1.

15. The polynucleotide of claim 14, wherein the polynucleotide sequence is codon optimized for the production of the encoded protein in eukaryotic host cells, bacteria, yeast or insect cells.

16. The polynucleotide of claim 14, which comprises the nucleic acid sequence of SEQ ID NO: 3.

17. An expression vector containing a polynucleotide of claim 14.

18. A host cell containing an expression vector of claim 17.

19. A method of producing the polypeptide-dimer of claim 1, comprising culturing a host cell comprising an expression vector comprising a polynucleotide encoding the polypeptide of claim 1, recovering and purifying the polypeptide-dimer from said host cell or the culture medium.

20. A composition containing a polypeptide-dimer of claim 1 and a pharmaceutically acceptable carrier.

* * * * *